United States Patent [19]
Herding et al.

[11] Patent Number: 5,618,412
[45] Date of Patent: Apr. 8, 1997

[54] FIXED-BED BIOREACTOR AND CARRIER BODY FOR PURIFYING FLUIDS

[75] Inventors: Walter Herding, Hahnbach; Peter Vogel, Ursula Poppenricht; Klaus Rabenstein, Hahnbach-Süss, all of Germany

[73] Assignee: Herding GmbH Entstaubungsanlagen, Amberg, Germany

[21] Appl. No.: 525,666

[22] PCT Filed: Mar. 24, 1994

[86] PCT No.: PCT/EP94/00945

§ 371 Date: Sep. 22, 1995

§ 102(e) Date: Sep. 22, 1995

[87] PCT Pub. No.: WO94/21566

PCT Pub. Date: Sep. 29, 1994

[30] Foreign Application Priority Data

Mar. 25, 1993 [DE] Germany .................. 43 09 779.0

[51] Int. Cl.⁶ .................. C02F 3/10; B29C 43/00; B29C 43/22
[52] U.S. Cl. .................. 210/150; 261/101; 261/DIG. 72; 264/122; 264/126; 264/DIG. 48
[58] Field of Search ............. 210/615, 618, 210/150, 151, 205; 261/101–107, DIG. 72; 264/126, 122, DIG. 48

[56] References Cited

U.S. PATENT DOCUMENTS

| | | | |
|---|---|---|---|
| 2,458,163 | 4/1944 | Hays | 210/2 |
| 3,231,490 | 1/1966 | Fry | 210/17 |
| 4,353,855 | 10/1982 | Garabedian | 264/122 |
| 4,409,170 | 10/1983 | Stofko | 264/122 |
| 4,439,317 | 3/1984 | Jarrell | 210/151 |
| 4,859,321 | 8/1989 | Iida | 210/150 |
| 5,419,831 | 5/1995 | Fuerst et al. | 210/151 |

FOREIGN PATENT DOCUMENTS

| | | |
|---|---|---|
| 137449 | 4/1985 | European Pat. Off. |
| 332907 | 9/1989 | European Pat. Off. |
| 314298 | 8/1982 | Germany |
| 4107406 | 9/1992 | Germany |

Primary Examiner—Thomas G. Wyse
Attorney, Agent, or Firm—Spencer & Frank

[57] ABSTRACT

A fixed-bed bioreactor with porous carrier bodies (14) for microorganisms. The carrier bodies are sheet-like structures with a small thickness in comparison with the carrier body surface. The carrier bodies are kept spaced apart by means of spacing bars (28), defining flow paths (36) between the carrier bodies. In a process for producing porous carrier bodies for microorganisms, plastics particles (70) are introduced into a moulding space (52) and bonded together therein by application of heat. With this process, an endless extrudate (46) of carrier body material may be produced, from which the individual carrier bodies may be cut off. Alternatively, the process may be carried out by means of a series of pairs of mould halves passing through a mould filling station and a heat supply station.

22 Claims, 7 Drawing Sheets

FIXED-BED BIOREACTOR AND CARRIER BODY FOR PURIFYING FLUIDS

The invention relates to a fixed-bed bioreactor for purifying fluids with the aid of microorganisms, containing a plurality of carrier bodies for microorganisms and flow paths for the fluid along the carrier bodies, with said carrier bodies having a porous structure with pores adapted to be penetrated by the fluid and to have microorganisms attach thereto.

Such fixed-bed bioreactors are known, with the carrier bodies having in particular a tubular shape. Deemed disadvantageous in this respect are the comparatively high manufacturing expenditure for the carrier bodies and the inconvenience of positioning the required number of carrier bodies in the bioreactor in a sensible relative arrangement It is the object of the invention to make available a fixed-bed bioreactor the carrier bodies of which can be manufactured in uncomplicated and efficient manner and can be positioned in particularly simple manner in the bioreactor in a sensible relative arrangement to each other.

To meet this object, the fixed-bed bioreactor according to the invention is characterized in that the carrier bodies are sheet-like structures having a small thickness in comparison with the carrier body surface; and in that the carrier bodies are kept spaced apart with the aid of spacing bars, thereby defining the flow paths between the carrier bodies.

The simplest form of a suitable sheet-like structure is that of a plate; substantially plate-shaped carrier bodies are in so far particularly preferred. However, configurations different from the exact planar plate shape can also be used in advantageous manner, especially configurations of the type of corrugated plates, with the course thereof relative to the main plate plane having a more rounded pattern or a more rectilinear and sharply bent pattern. It is, however, preferred when the shape of the particular carrier body—seen roughly and in its entirety—is plate-shaped in the last-mentioned cases as well, since the carrier bodies can then be installed in the bioreactor in particularly advantageous manner.

The material thickness of the carrier bodies does not have to be constant for the entire particular carrier body. However, it is preferred when the particular carrier body at all locations has at least substantially the same material thickness. The term "carrier body surface" in a strictly plate-shaped carrier body is understood to be the size of one face of the carrier body, and, in case of corrugated plate-like structures, the size of the respective face that may be conceived as having been created by corrugation of the planar face of a plate.

The carrier bodies, either on one or on both carrier body surfaces, preferably are formed integrally with spacing bars. In this case, the carrier bodies can be placed adjacent each other in especially simple manner by having the spacing bars abut the adjacent carrier body or bodies, either directly or via spacing bars of the adjacent carrier bodies. However, it is possible as well to manufacture the spacing bars separately from the carrier body. In this case, the arrangement of the carrier bodies in the bioreactor takes place in the form of an alternating sequence of carrier bodies and spacing bars.

It is preferred to unite a plurality of carrier bodies in the form of a carrier unit package and to install it in the bioreactor as an interconnected package. This is effected in particular by joining the integral spacing bars of a particular carrier body with the adjacent carrier body on one side thereof or with the adjacent carrier bodies one both sides thereof. Alternatively, this may be effected by attaching separately produced spacing bars to a carrier body, attaching the adjacent carrier body to the spacing bars, attaching further spacing bars on the "free" side of the last carrier body, and so on. For connecting the spacing bars to carrier bodies or also for connecting spacing bars of adjacent carrier bodies to each other, adhesive bonding or welding are particularly preferred.

It is pointed out that the spacing bars indeed have preferably the shape of elongate material strips, however, it is irrelevant for the function of the spacing bars and the bioreactor that these are continuous spacing bars for each carrier body. For example, the spacing bars may have spaced apart openings or be composed of a series of spaced apart spacing members. The spacing bars may be solid or porous. They do not have to be, but may be, made from the same material as the carrier bodies.

The carrier bodies preferably consist mainly of plastics particles connected by the application of heat. Polyethylene particles are especially preferred, however, with other plastics materials being suitable as well. The carrier bodies preferably contain in addition particles of fine porosity, such that an overall construction of the carrier bodies with larger pores e.g. between the plastics particles and smaller pores within the fine-porosity particles results. The microorganisms will then attach themselves not only in the coarser pores, but also in the finer pores. Suitable fine-porosity particles consist e.g. of coarsely ground expanded clay, activated carbon or other organic substances. What is important is that the carrier bodies in their entirety, i.e. inclusive of the microporous particles, can be penetrated by the fluid to be purified. The carrier bodies thus are structures with open pores which, possibly inclusive of the fine-porosity particles, are adapted to be flown through by the fluid.

The carrier bodies furthermore may contain additives, with nickel being indicated as an example, having a catalytic effect for the processes of life of the microorganisms.

A further subject matter of the invention are carrier bodies for fixed-bed bioreactors for purifying fluids with the aid of microorganisms, with the carrier body having a porous structure with pores adapted to be penetrated by the fluid and to have the microorganisms attach thereto, characterized in that the carrier body is a sheet-like structure with a small thickness in comparison with the carrier body surface; and in that the carrier body has spacing bars formed integrally therewith for defining the distance to an adjacent carrier body.

The aspects outlined hereinbefore as well as the aforementioned preferred developments hold analogously also for the carrier bodies according to the invention.

The invention relates furthermore to a process for producing carrier bodies of porous structure adapted to have microorganisms attach thereto, said process comprising the following steps:

(a) providing plastics particles;

(b) introducing the plastics particles into a moulding space; and (c) supplying heat to the plastics particles contained in the moulding space such that the plastics particles are bonded together forming the porous carrier body structure.

According to the inventions, this manufacturing process is to be carried out in such a manner that a continuous or semi-continuous or an assembly line-like, cycled intermittent operation results.

According to a first solution provided according to the invention with respect to the process, the production process is characterized in (d) that an endless extrudate of carrier body material is withdrawn from the moulding space; and in (e) that the individual carrier bodies are separated from the extrudate, e.g. by cutting, sawing or the like.

When the moulding space is designed and operated in terms of the process such that it provides a continuous extrudate shape, preferably by limiting the moulding space on two opposite sides by endless revolving belts or by rotary rolls of sufficient diameter and when, in addition thereto, the plastics particles are fed to the moulding space in continuous or quasi-continuous manner, a continuous production process is realized.

Alternatively, it is possible to limit the moulding space by mould parts adapted to be opened and closed, in particular mould halves, and to introduce the plastics particles when the mould parts are in their respective closed condition. This "batchwise" introduction does not exclude that an endless extrudate of carrier body material is formed in stepwise and intermittent manner. Such a production process may be referred to as a semi-continuous one.

The invention provides furthermore an assembly line-like, cycled process for producing separate carrier bodies which, in addition to process steps (a), (b) and (c) mentioned hereinbefore, is characterized by the further steps (d) that the particular moulding space is confined by a first and a second mould half;

(e) that a number of the first mould halves is mounted on a first conveyor and a number of the second mould halves is mounted on a second conveyor;

(f) that the mould halves in the closed condition thereof are adapted to be moved through a station for introduction of the plastics particles and through a station for the supply of heat to the introduced plastics particles; and (g) that the mould halves, due to the design of said first and second conveyors, are closed and opened automatically.

For making shorter the dwell time in the moulding space necessary for the bonding together of the plastics particles, the plastics particles may be heated prior to introduction into the moulding space. There is a number of technical possibilities for supplying heat to the plastics particles contained in the moulding space. To be mentioned as preferred examples are the supply of heat by heating confining surfaces of the moulding space and/or microwaves and/or heat radiation and/or addition of preheated fine-porosity particles.

The production processes according to the invention, also the continuous ones, permit a particularly efficient production of carrier bodies having spacing bars integrally formed thereon when the moulding space confining means are designed in corresponding manner. In accordance with a particularly preferred development of the processes according to the invention, it is to be possible to manufacture carrier bodies having spacing bars of different height since, depending on the fluid to be purified and depending on the microorganisms employed for purification, flow paths of different dimensions between the carrier bodies are advantageous. To this end, it is advantageously possible to employ exchangeable moulding space confining means. Another preferred alternative consists in providing a moulding space confining means having one or more grooves (for forming the spacing bars), with the groove depth corresponding to the maximum spacing bar height to be produced. When carrier bodies with spacing bars of lower height are to be made, material inserts may be disposed in the grooves, reducing the effective groove depth.

The production processes according to-the invention are also suitable for making carrier bodies containing microporous particles, as pointed out hereinbefore. To this end, it is merely necessary to add such microporous particles, at best in evenly distributed manner, to the plastics particles introduced in the moulding space.

The bioreactor according to the invention and the carrier bodies according to the invention, respectively, are suitable for treating a multiplicity of fluids. Typical examples thereof are, in particular highly polluted, sewage or waste water of a large number of different origins (in particular waste water with organic pollutions, e.g. from slaughterhouses, breweries, dairies and from food processing industrial plants in general). The bioreactor preferably is a bioreactor operating in anaerobic manner, but may also be a bioreactor operating in anoxic or aerobic manner. It is possible to use either microorganisms with anabolic metabolism, i.e. directed to the decomposition of specific products or pollutants. Or it is possible to make use of microorganisms with catabolic metabolism, i.e. directed to the formation of specific desired metabolic products, e.g. production of antibiotics, alcohol etc. The treatment of gases and liquids may be combined with each other.

As regards the production processes for carrier bodies according to the invention, it is to be mentioned in addition that the carrier bodies produced or the carrier body extrudate produced, respectively, are normally cooled prior to and/or during and/or after discharge thereof from the moulding space, e.g. by blowing air thereagainst.

The invention and further developments of the invention will be elucidated in more detail hereinafter by way of embodiments shown schematically in the drawings in which FIG. 1 shows a sewage purifying plant comprising a fixed-bed bioreactor;

Figure 1:
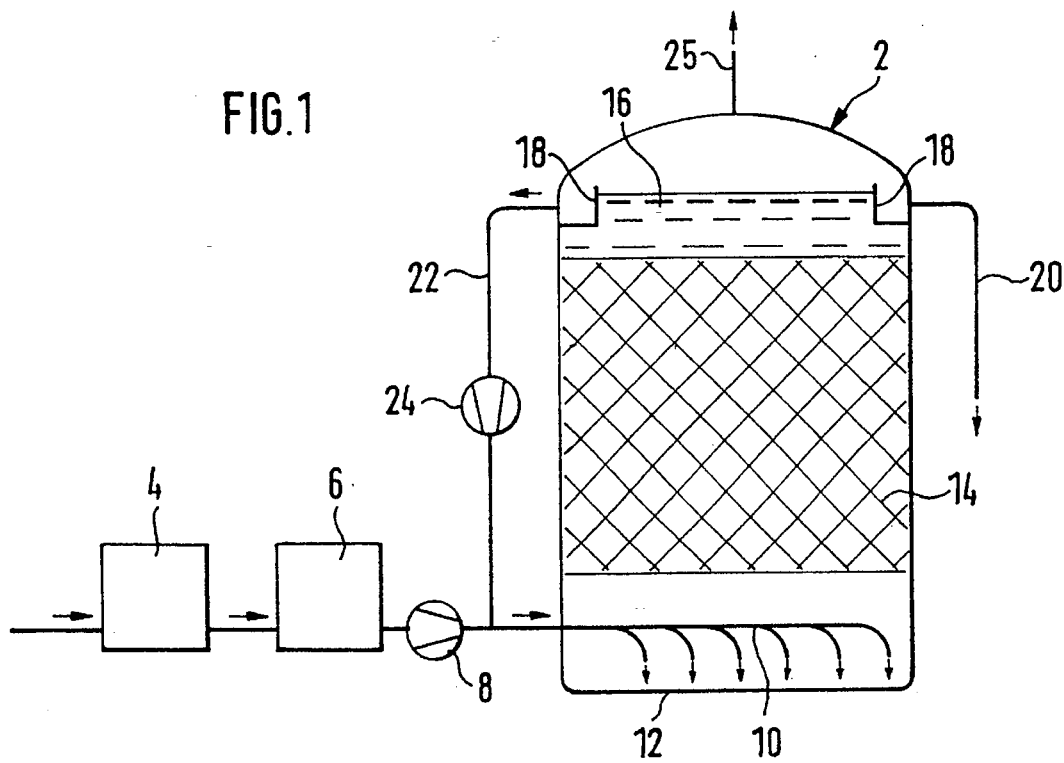

The plant for the biological treatment of sewage or waste water, as shown in FIG. 1 with its main constituent parts, consists in essence of a fixed-bed bioreactor 2 upstream of which are disposed a container 4 with quasi-continuous or semi-continuous passage for neutralization of the sewage to be treated and a heat exchanger 6 bringing the sewage to be treated to a temperature that is favourable for the biological treatment. By means of a pump 8 and a pipe distribution system 10, the sewage is evenly distributed over the floor 12 of the bioreactor 2 and is pumped into the bioreactor 2 in the form of downwardly directed beams in the lower portion thereof. Bioreactor 2 on the whole has the configuration of an upright cylinder, with the upper closure wall being possibly slightly curved in upward direction. As an alternative, bioreactor 2 may be of square or rectangular cross-section. Preferred materials for the bioreactor 2 are stainless steel and, in particular in case of very large volume, concrete.

Above the pipe distribution system 10, bioreactor 2 has multiplicity of carrier bodies 14 disposed therein, as will still be described in more detail further below. Above the carrier bodies 14, bioreactor 2 contains therein a quiescent zone 16 with a sludge sedimentation space. An outflow pipe 20 leaves bioreactor 2 behind an overflow weir 18. Shown furthermore is a recirculation line 22 having a pump 24 installed therein. Through said recirculation line, sewage can be withdrawn from the quiescent zone 16 and supplied to the pipe distribution system 10. By recirculation of part of the sewage that has already passed through the arrangement of the carrier bodies 14, the average dwell time of the sewage in the bioreactor can be enhanced. Gas produced can flow off through a central upper conduit 25.

Figure 2B:
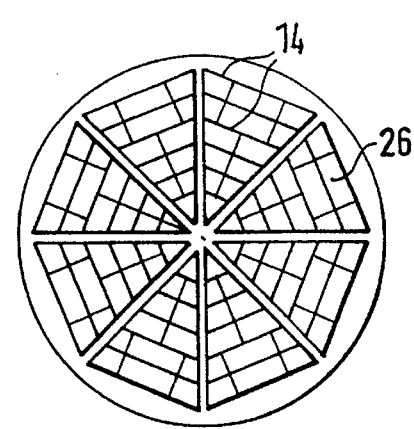
FIG. 2b shows a horizontal cross-section of a modified bioreactor.
Figure 2A:
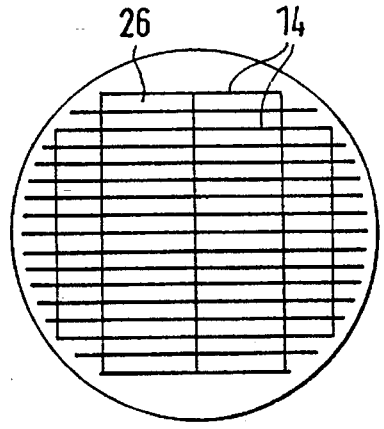
FIG. 2a shows a horizontal cross-section of the bioreactor of FIG. 1.

It can be seen in FIG. 2a that the carrier bodies 14 have the configuration of planar plates placed in upright positions. The carrier bodies are arranged parallel to each other and— as measured in horizontal direction—are of different width so that the interior of bioreactor 2 can be utilized as completely as possible. The sewage flow in bioreactor 2 is from the bottom upwardly along the faces of the plate-shaped shaped carrier bodies 14, through the distance spaces 26 between two adjacent carrier bodies 14 each. As an alternative, one could also construct a bioreactor having a sewage flow from the top downwardly. The carrier bodies 14 do not have to be as wide as the bioreactor 2, but could De subdivided into a plurality of juxtaposed carrier bodies.

In the modification according to FIG. 2b, a plurality of parallel carrier bodices 14 each form a triangular carrier body package. A plurality of carrier body packages is circumferentially placed adjacent each other such that a total configuration of nearly circular outer circumference with polygonal cross-section results, with the carrier bodies 14 each extending tangentially.

Figure 3:
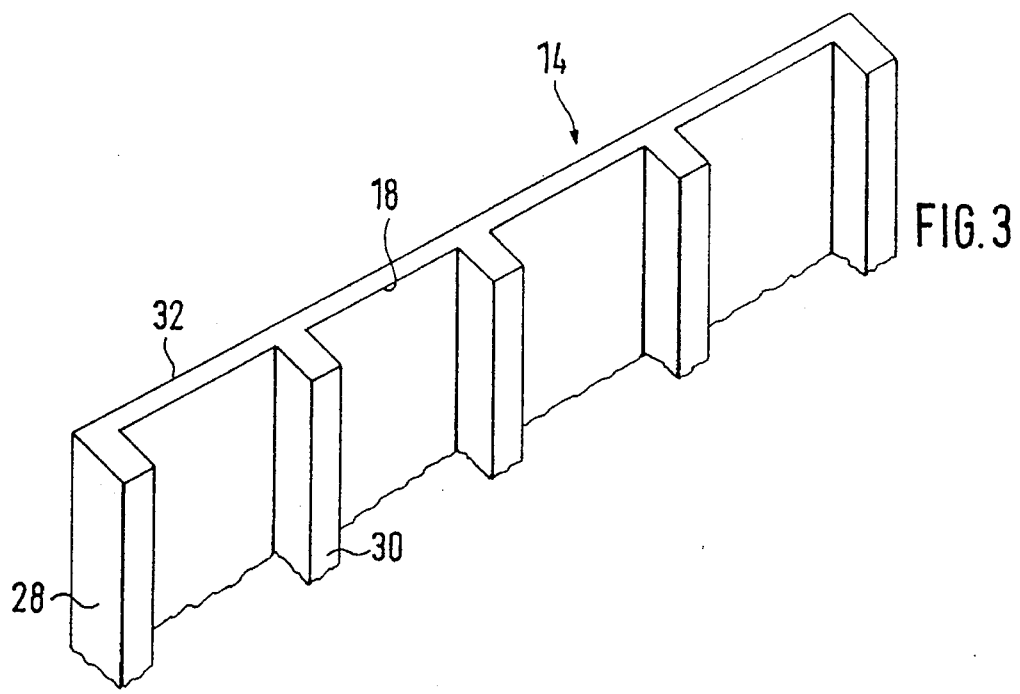
FIG. 3 shows a perspective view of a carrier body having integral spacing bars, of the bioreactor of FIG. 1.

FIG. 3 illustrates the construction of a carrier body in more detail. Integrally formed, projecting spacing bars 28 are provided on a face 18 of carrier body 14. Spacing bars 28 extend vertically when carrier body 14 is installed in bioreactor 2. The end surfaces 30 of all spacing bars 28 are located in a common plane. On the opposite face 32, carrier body 14 is not provided with spacing bars 28, but is completely planar.

Figure 4:
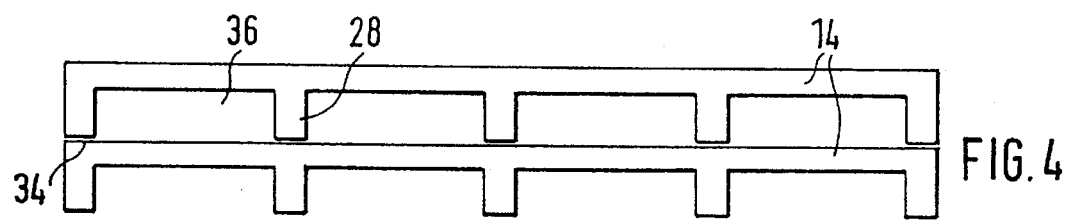
FIG. 4 shows a horizontal cross-section of an arrangement of two carrier bodies according to FIG. 3.

FIG. 4 shows the manner in which carrier bodies according to FIG. 3 may be placed parallel against each other so as to form an arrangement of a multiplicity of carrier members 14. To this end, the end surfaces 30 of the spacing bars 28 of the, in FIG. 4, upper, first carrier body are placed adjacent face 32 of the, in FIG. 4, lower, second carrier body 14, and a firm connection is then established at the resulting contact areas 34 between the two adjacent carrier bodies 14, preferably by adhesive bonding or by welding. This arrangement is continued analogously in downward direction in FIG. 4 until a package of e.g. ten to 100 interconnected carrier bodies 14 is formed.

It is to be understood that the horizontal width of the carrier bodies 14 as seen in FIG. 4 may vary so as to adapt the overall configuration of the carrier package e.g. to a cylindrical bioreactor 2 as shown in FIG. 2. It is possible to arrange several carrier body packages according to FIG. 4 in bioreactor 2 in juxtaposed manner. It is to be understood, furthermore, that this length of the carrier bodies 14 is selected to match the height of the particular bioreactor 2.

Flow paths 36 of substantially rectangular cross-section are defined such that they are confined each on two opposite sides by spacing bars and on the two other opposite sides by carrier body surfaces 18 and 32, respectively. It is pointed out that spacing bars 28 do not necessarily need to have a continuous ledge-shaped configurations as depicted in FIG. 3. Certain transverse flows from flow path 36 to flow path 36 have no negative effect. What is important in terms of function is mainly that the carrier bodies 14 are positioned in stable and spaced apart manner by means of the spacing bars 28.

Figure 5:
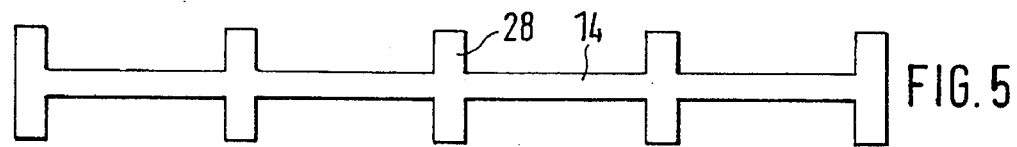
FIG. 5 shows a horizontal cross-section of a modified embodiment of a carrier body with integral spacing bars.

FIG. 5 shows a modification in which carrier bodies 14 each are provided on both faces thereof with integral spacing bars 28. Upon abutting placement of an adjacent carrier body 14, spacing bar 28 is positioned in abutment with spacing bar 28.

Figure 6:
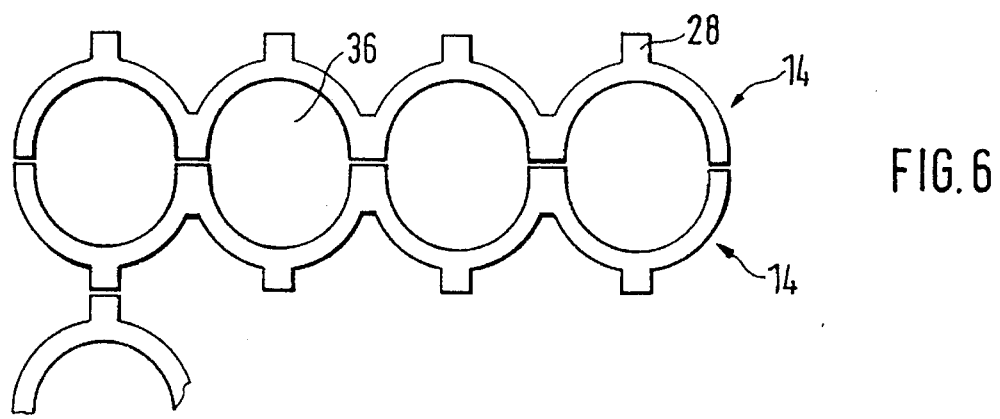
FIG. 6 shows a horizontal section of a further modified embodiment of a carrier body with integral spacing bars, in the form of an arrangement of several carrier bodies.

FIG. 6 shows a further example of a multiplicity of possible modifications for the geometry of the carrier bodies 14. Shown therein is a modification that may be referred to as corrugated plate in which about semi-circular bulges equally follow each other in succession. Here, too, one can see spacing bars 28 integrally formed on the two "large area sides" of carrier bodies 14. Adjacent carrier bodies 14 abut each other in the form of a mirror image. Flow paths 36 of two geometries are formed, namely a substantially circular one and a substantially square one with inwardly bulging confining walls.

Figure 7:
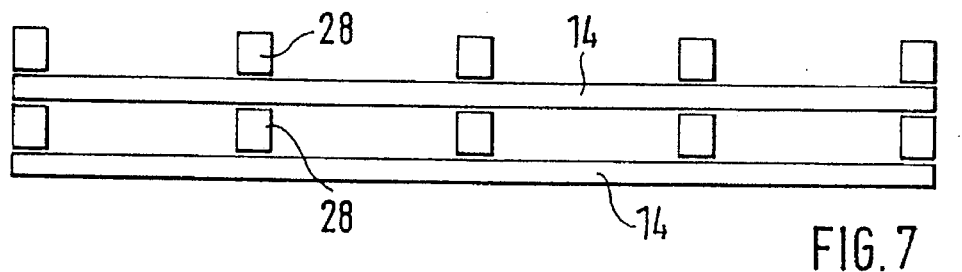
FIG. 7 shows a horizontal section of an arrangement of a plurality of carrier bodies having separate spacing bars disposed therebetween.

FIG. 7 illustrates a modification in which spacing bars 28 are not formed integrally on the plate-shaped carrier bodies 14, but are provided in the form of separate strip-shaped members. Spacing bars 28 are connected to the two adjacent carrier bodies each, for example by means of adhesive or by welding, so that in total a carrier body package analogous with the embodiment of FIG. 4 is formed.

Figure 8:
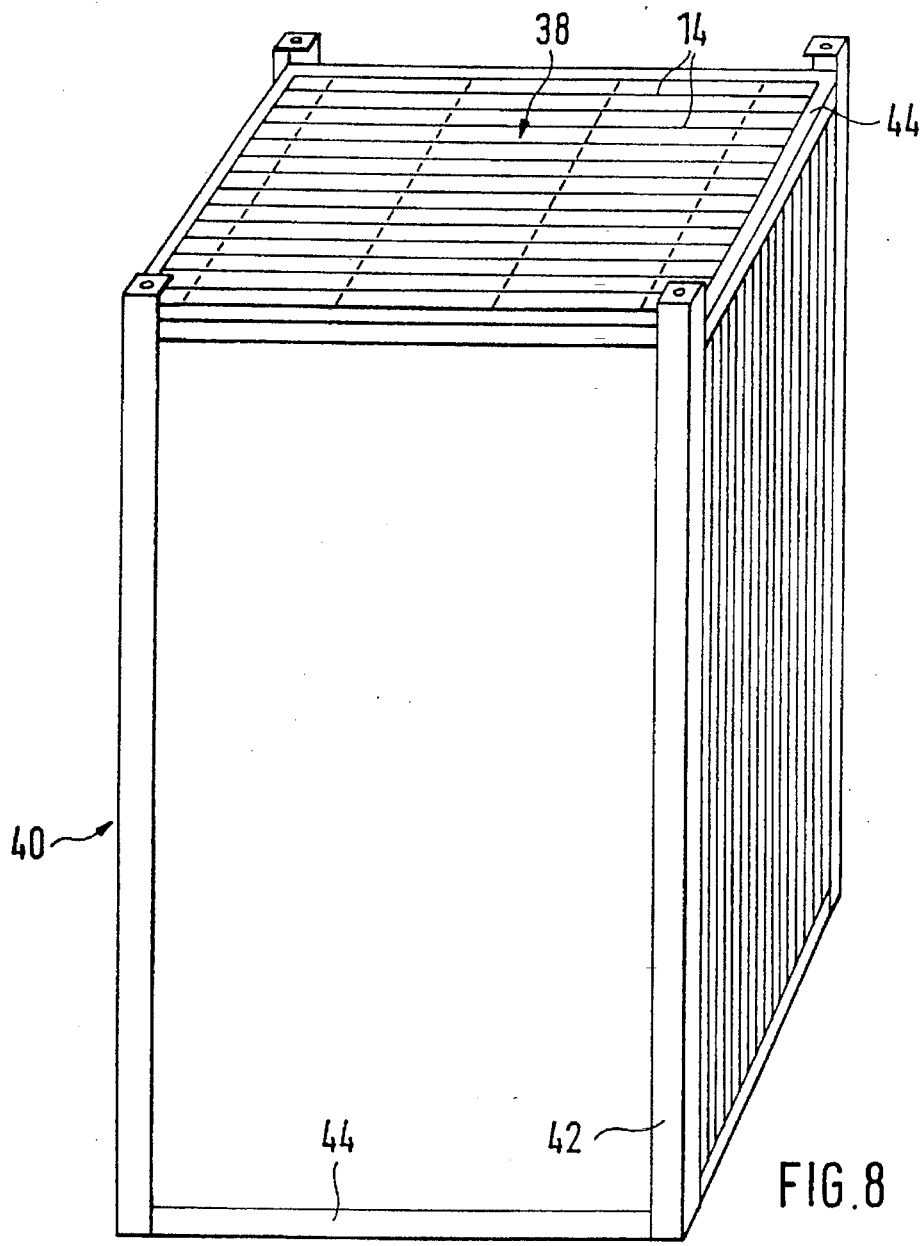
FIG. 8 shows a carrier body package composed of a plurality of carrier bodies.

FIG. 8 shows the manner n which a carrier package 38 is mounted in a kind of frame 40. Frame 40 consists in essence of four vertical angle sections 42 at the corners of the carrier body package 38. These angle sections 42 are connected at the top and at the bottom by four connecting rods 44 each. The carrier body package 38 is installed in bioreactor 2 in this overall configuration, e.g. With frame 40 resting on the floor of bioreactor 2. In case of relatively high bioreactors 2, several such carrier body packages 38 may be disposed one above the other. A typical height of a carrier body package 38 is between 1 and 2 m. The horizontal dimensions may be, for example, 0.5 to 2 $m^2$.

The carrier bodies 14 preferably consist of plastics particles, e.g. particles of polyethylene of average density, bonded together by the application of heat.

The plastics particles typically have a particle size that is mainly in the range from 200 to 3000 μm, with the by far predominant part of the particles having a particle size of 630 to 1600 μm. Moreover, the carrier body 14 contains coarsely ground particles of expanded clay, which a microporous per se. The size of the pores between the plastics particles is 0.1 to 5000 μm, with the by far predominant part of the pores being in the pore size range from 100 to 500 μm. The pores in the expanded clay particles are on the average considerably smaller.

Figure 9:
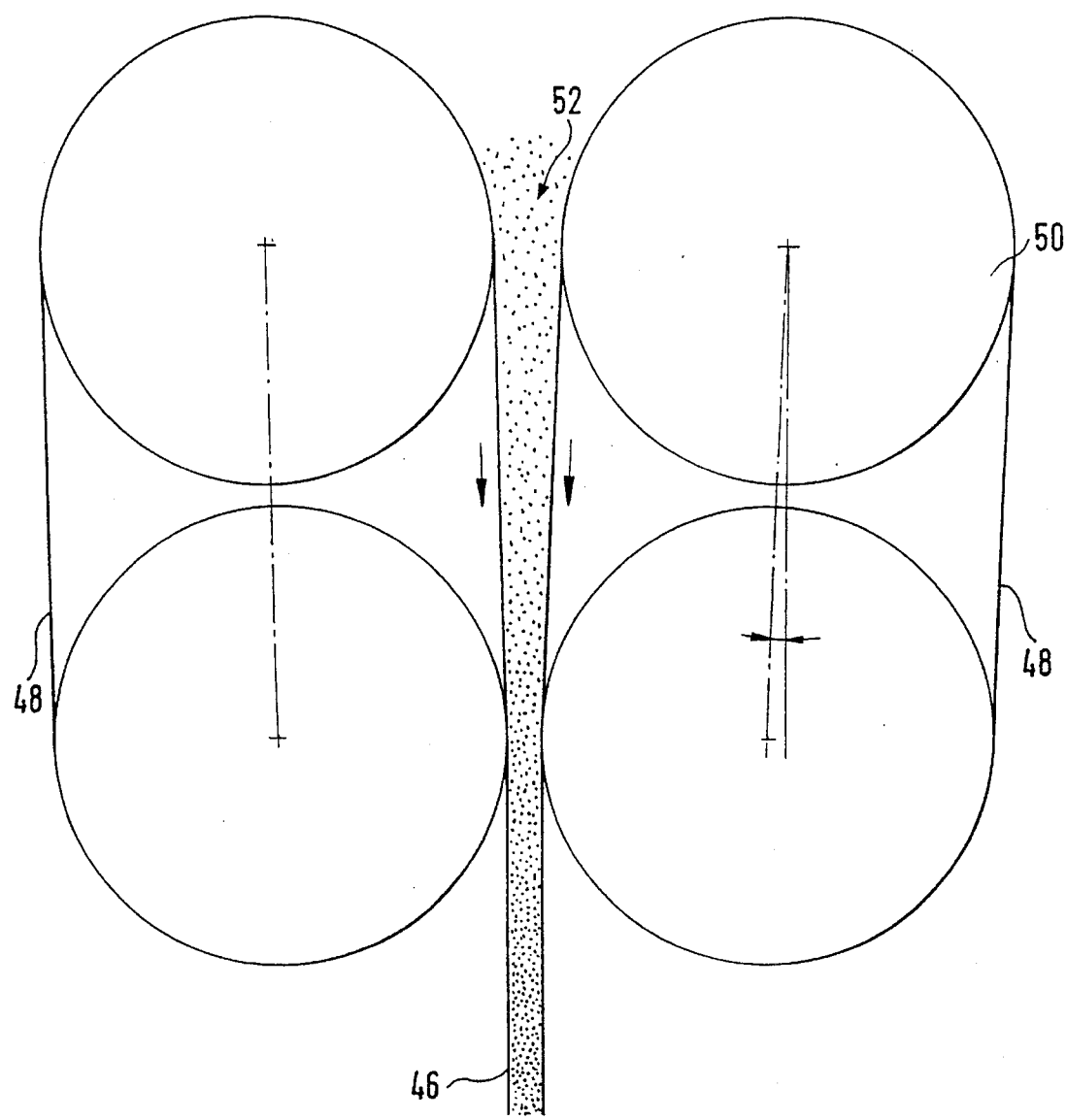
FIG. 9 shows the moulding space of an apparatus for making carrier bodies in a continuous operation.

FIG. 9 illustrates the manner in which an extrudate 46 of porous carrier body material can be produced in continuous manner. There are provided two endless metal belts 48 each passed around two spaced apart rollers 50. In the center of the arrangement, the two metal belts 48 extend almost parallel to each other, but at the bottom of FIG. 9 between the two lower rollers with a slightly smaller distance than at the top in FIG. 9 between the two upper rollers. The raw material, namely plastics particles and coarsely ground particles of expanded clay, are introduced from above into the—roughly speaking—funnel-shaped space between the two belts 48 extending there around the two upper rollers 50. Belts 48 are heated, and the length of the contact between the plastics material and the two belts 48 is dimensioned and matched to the movement speed of the belts 48 such that the time is sufficient for making the plastics particles tacky at their surface by increasing the temperature and to cause them to bond together. A temperature range suitable therefor is 160° to 190 ° C. Upon leaving the pair of belts 48, the extrudate is cooled. Further below, the extrudate is cut transversely of its longitudinal direction so as to form the individual carrier bodies 14.

Figure 10:
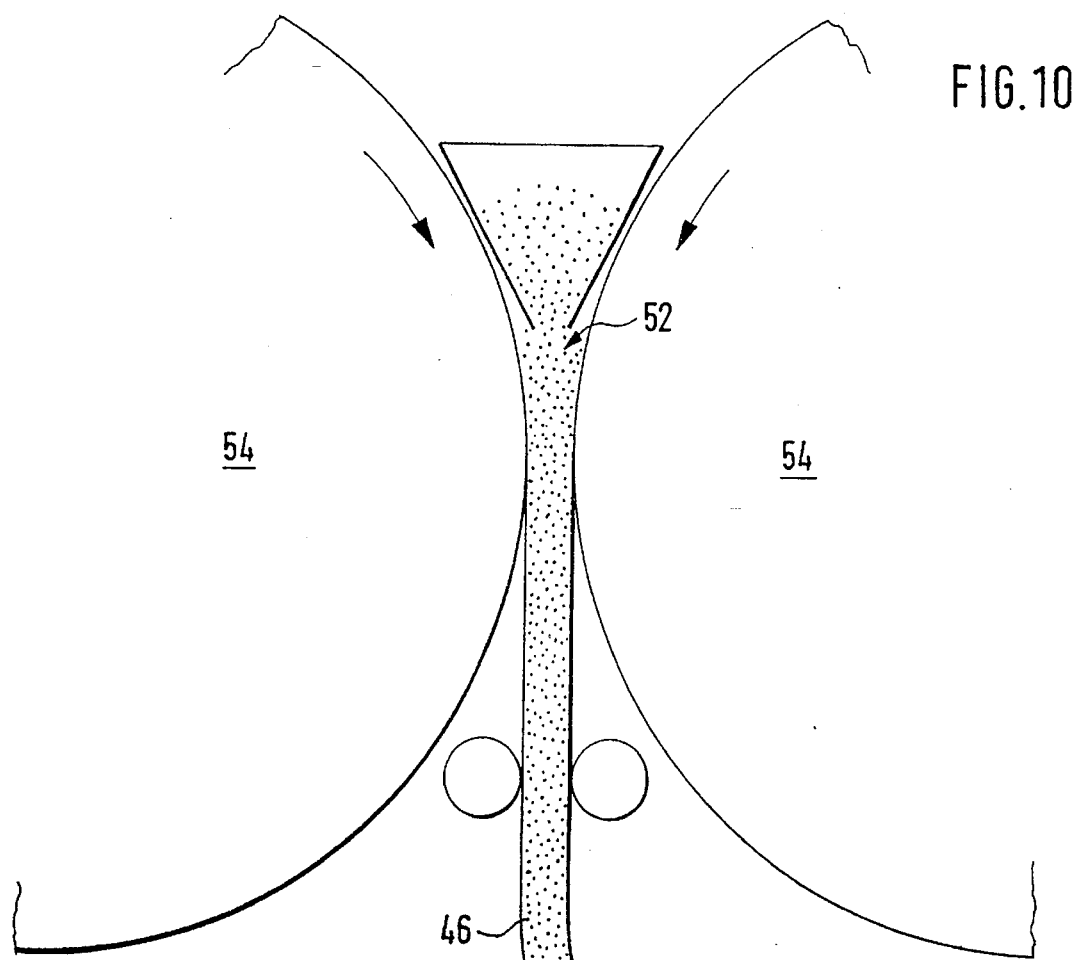
FIG. 10 shows the moulding space of an additional embodiment of an apparatus for making carrier bodies in a continuous operation.

FIG. 10 shows a modification in which the two belts 48 are replaced by a pair of rollers 54. The operation is basically the same as described hereinbefore.

Figure 11:
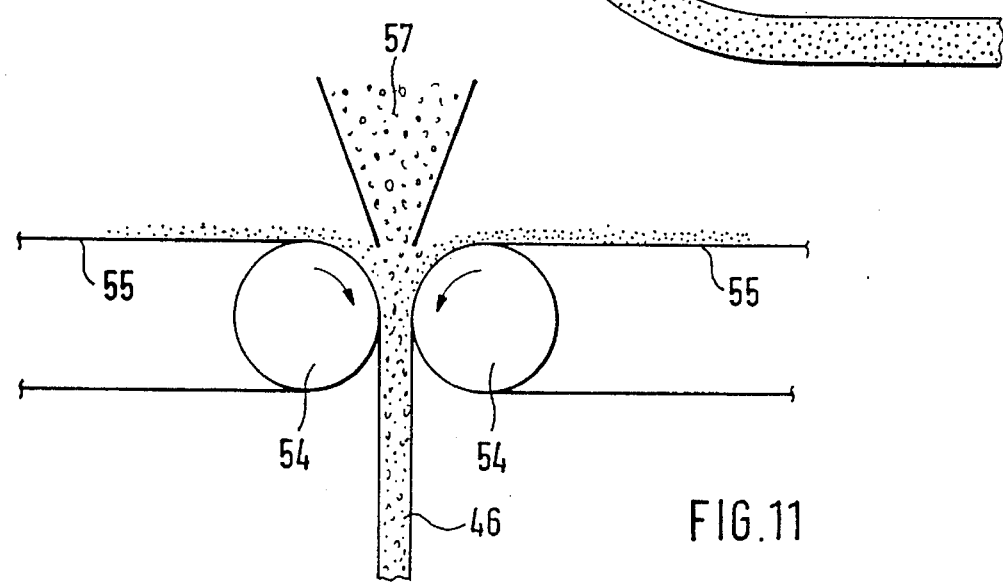
FIG. 11 shows the moulding space of a still further embodiment of an apparatus for making carrier bodies in a continuous operation.

FIG. 11 shows a modification similar to the embodiment of FIG. 10, in which however each of the two rollers 54 is an end deflection roller of a horizonal endless conveyor belt 55 of metal. The plastics particles are conveyed on the conveyor belts 55 to the moulding space between the two rollers 54. From above, coarsely ground particles of expanded clay drop from a supply hopper 57 into the "mouding gap". The expanded clay particles are preheated to a temperature of e.g. more than 200° C. and introduce so much heat into the moulding space that the bonding together of the plastics particles takes place there with simultaneous integration of the expanded clay particles.

Figure 12:
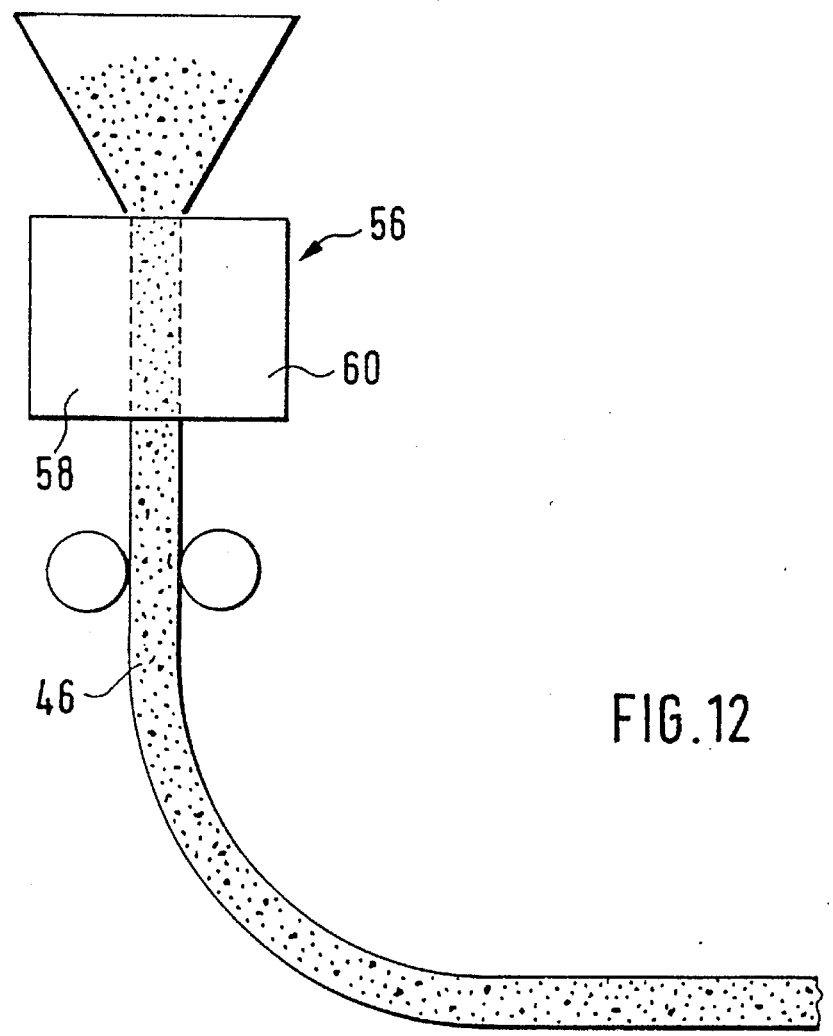
FIG. 12 shows a schematic view of an apparatus for making carrier bodies in a semi-continuous operation.

FIG. 12 illustrates a process which, with respect to the moulding operation of extrudate 46, takes place in a stepped sequence. Instead of the pair of belts 48 and rollers 54, respectively, there is provided a mould 56 consisting of two mould halves 58 and 60. With the mould halves 58, 60 in the closed condition, the raw material is introduced from above into the mould cavity. Upon introduction, the mould halves 58, 60 can still be moved somewhat closer towards each other, so as to exert pressure on the mould contents. At this time, the extrudate 46 to be formed is stationary. Heat is supplied to the mould contents for bonding the plastics particles together. The mould halves 58, 60 are then slightly opened and the extrudate 46 to be formed is withdrawn downwardly by a length corresponding substantially to the height of mould 46. Mould 56 is closed again, and the process is repeated.

Figure 13:
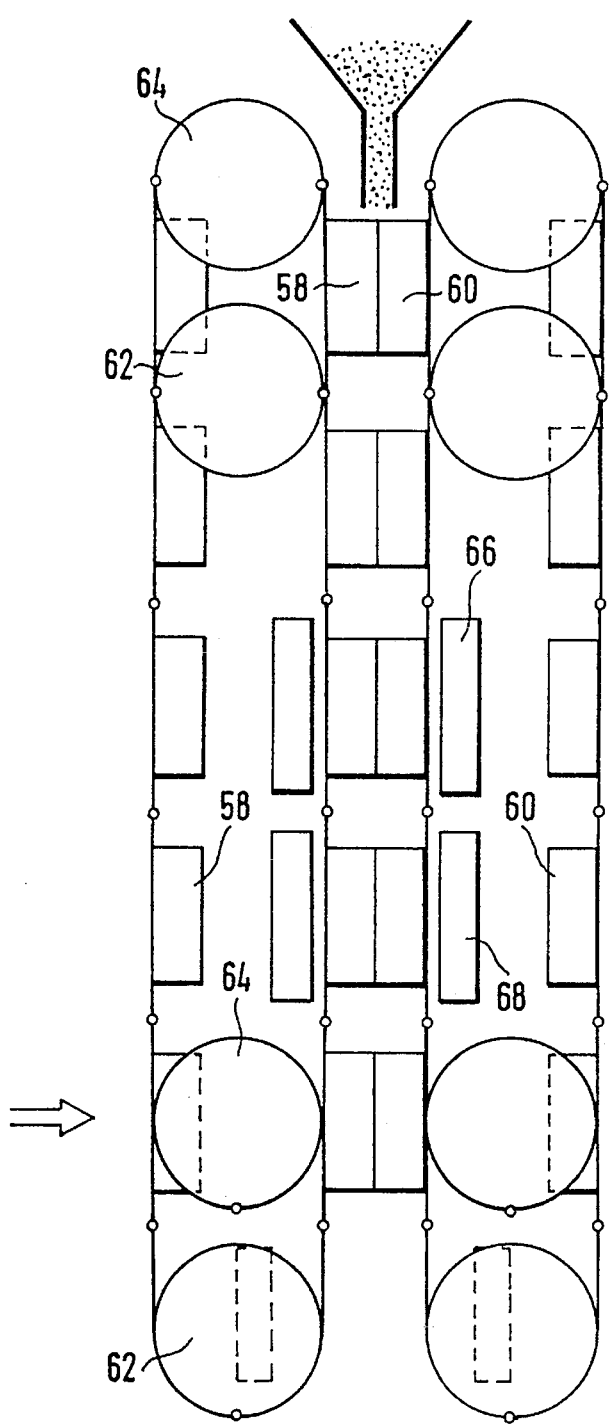
FIG. 13 shows a schematic view of an apparatus for making carrier bodies in a cycled, intermittent operation.
Figure 13A:
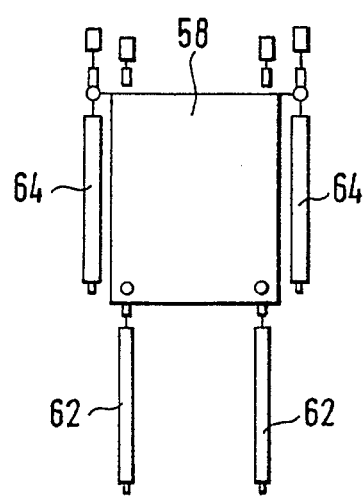
FIG. 13a shows a side view of part of the structure depicted in FIG. 13, as viewed in the direction of the arrow to the left of FIG. 13.

FIG. 13 shows a production process which does not result in a continuous extrudate 46 of carrier body material, but in cycled, intermittent manner provides a sequence of separate carrier bodies 14. Left-hand mould halves 58 analogous with the left-hand mould half 58 of FIG. 12 are attached in series on two conveyors which are each in the form of a pair endless conveyor chains. The lower ends of the mould halves on as also shown in FIG. 13a, the left side in FIG. 13 are attached to a pair of conveyor chains deflected via lower chain wheels 62, whereas the, in FIG. 13, upper ends of the left-hand mould halves in FIG. 13 are mounted on an additional chain pair whose chains are deflected by upper deflection wheels 64. On the right-hand side of the plant shown in FIG. 13, the same arrangement, in a mirror image, is provided for right-hand mould halves 60. With this construction, a pair of a left-hand mould half 58 and a right-hand mould half 60 closes in the upper region of the plant. The raw material is filled in from above. The endless chains along with the mould halves travel continuously downwardly in FIG. 13, passing a heating station 66 and thereafter a cooling station 68. Further below, the mould halves move apart so that the finished carrier body can be removed therefrom. The sequence of operations may also take place in stepped or intermittent manner such that the individual moulds each stop in the material introduction station, in the heating station, in the cooling station and in the discharge station. In the material introduction station, the mould may be vibrated for compaction of its contents.

It is to be understood that in the embodiments of FIGS. 9, 10 and 11, the moulding space is closed laterally, i.e. both in front of and to the rear of the drawing plane. For examples, plates are attached there between which the belts 48 or the rollers 54 run with close lateral play.

As was pointed out already several times, the plastics particles to be bonded together by the application of heat must have a temperature suitable therefor in the moulding space (in case of polyethylene particles e.g. in the temperature range from 160° to 190° C.). The most preferred possibilities for obtaining such temperatures in the moulding space are, either alone or in combination:

heating at leat part of the confining areas of the moulding space, i.e., for example heating of the belts 48 or the rollers 54;

preheating the plastics particles and/or the expanded clay particles. Preheating of the expanded clay particles is especially efficient since these may be preheated to a higher temperature before addition to the plastics particles and since they have a relatively high heat capacity;

other supply of heat to the contents of the moulding space, preferably by blowing hot air therethrough, heating by microwaves and the like. In the embodiments according to FIGS. 9, 10 and 11, the last-mentioned mode of heating may be carried out e.g. perpendicularly to the drawing plane.

The preferred weight ratio between plastics particles and fine-porosity particles is 10 to 65%, preferably 30 to 55%, plastics particles, remainder fine-porosity particles.

Figure 14:
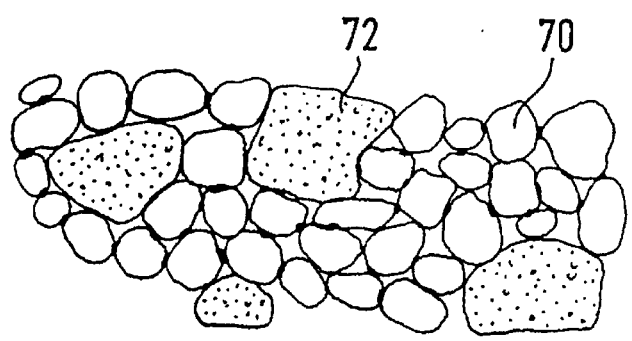
FIG. 14 shows a section of a carrier body according to the invention.

FIG. 14 illustrates the manner in which the plastics particles 70 and the fine porosity particles 72 are present in the finished carrier body 14.

It has already been mentioned that the bioreactor 2 according to the invention is suitable for treating either liquids or liquids in the presence of gases. In both cases, the main flow of the liquid to be treated or of the gas to be treated may be preferably from the bottom upwardly or from the top downwardly. However, it is also possible to treat in a bioreactor 2 both a liquid and a gas at the same time. Liquid and gas may flow therein either in co-current flow or in counter-flow. By way of FIG. 1 it is conceivable easiest that in addition to the sewage distribution system 10 a gas distribution system is provided in the lower portion of bioreactor 2. Sewage and gas flow upwardly in a co-current flow. This is at the same time an example for an aerobic water treatment.

The continuous processes according to FIGS. 9, 10 and 11 may also be used without any problems for producing carrier bodies 14 having integral spacing bars 28, by providing e.g. belts 48 or rollers 54 with corresponding recesses in longitudinal direction and circumferential direction, respectively.

We claim:

1. A fixed-bed bioreactor for purifying fluids with the aid of microorganisms, containing a plurality of carrier bodies for microorganisms and flow paths for the fluid along the carrier bodies, with said carrier bodies being sheet-like structures with a small thickness in comparison with the carrier body surface and having porous structure with poles adapted to be penetrated by the fluid and to have microorganisms attach thereto, and being composed with plastics particles bonded together by the application of heat, said carrier bodies being spaced apart with the aid of spacing bars defining the flow paths between the carrier bodies; and said spacing bars being formed integrally with the plastics material of a respectively associated carrier body.

2. A fixed-bed bioreactor according to claim 1, wherein a plurality of carrier bodies are united to form a carrier body package by mutual connection thereof with inclusion of the spacing bars.

3. A fixed-bed bioreactor according to claim 2, wherein said carrier bodies are united by adhesive bonding or by welding.

4. A fixed-bed bioreactor according to claim 1, wherein said carrier bodies each have substantially the shape of a planar plate with integral spacing bars.

5. A fixed-bed bioreactor according to claim 1, wherein the carrier bodies contain fine porosity particles.

6. A carrier body for fixed-bed bioreactors for purifying fluids with the aid of microorganims, said carrier body being a sheetlike structure with a small thickness in comparison with the carrier body surface and having a porous structure with pores adapted to be penetrated by the fluid and to have microorganisms attach thereto, and being composed with plastics particles bonded together by the application of heat, said carrier body having spacing bars formed integrally with its plastics material for defining the distance to an adjacent carrier body.

7. A carrier body according to claim 6, and having substantially the shape of a planar plate with spacing bars projecting therefrom.

8. A carrier body according to claim 6, and containing find-porosity particles.

9. A process for producing carrier bodies of porous structure adapted to have microorganisms attach thereto, said process comprising the following steps:

(a) providing plastics particles;

(b) introducing the plastics into a moulding space; and (c) supplying heat to the plastics particles contained in the moulding space such that the plastics particles are bonded together forming the porous carrier body structure, (d) the contents of the moulding space being entrained by movement of movable moulding space confining means in the direction towards a discharge end of the moulding space and in the course of the entraining movement being bonded together to form the porous carrier body structure by supply of heat.

10. A process according to claim 9, wherein the moulding space is confined on two opposed sides by endless revolving belts.

11. A process according to claim 9, wherein the moulding space is confined on two opposed sides by rollers.

12. A process according to claim 9, wherein the plastics particles are introduced continuously into the moulding space.

13. A process according to claim 9, wherein the plastics particles are preheated prior to introduction into the moulding space.

14. A process for producing carrier bodies of porous structure adapted to have microorganisms attach thereto, said process comprising the following steps:

(a) providing plastics particles;

(b) introducing the plastics particles into a moulding space; and (c) supplying heat to the plastics particles contained in the moulding space such that the plastics particles are bonded together forming the porous carrier body structure, (d) the particular moulding space being confined by a first and second mould half;

(e) a number of the first mould halves being mounted on a first conveyor and a number of the second mould halves being mounted on a second conveyor;

(f) the mould halves in the closed condition thereof being adapted to be moved through a station for introduction of the plastics particles and through a station for the application of heat to the introduced plastics particles; and (g) the mould halves, being closed and opened automatically due to the design of said first and second conveyors.

15. A process according to claim 9, wherein the moulding space is designed so as to produce carrier bodies with spacing bars integrally formed thereon.

16. A process according go claim 14, wherein the moulding space is designed so as to produce carrier bodies with spacing bars integrally formed thereon.

17. A process according to claim 15, wherein the confining means of the moulding space can be exchanged or, if necessary, can be equipped with material inserts so as to be able to produce carrier bodies having spacing bars of different height.

18. A process according to claim 16, wherein the confining means of the moulding space can be exchanged or, if necessary, can be equipped with material inserts so as to be able to produce carrier bodies having spacing bars of different height.

19. A process according to claim 9, wherein fine-porosity particles are added to the plastics particles.

20. A process according to claim 14, wherein fine-porosity particles are added to the plastics particles.

21. A process according to claim 9, wherein heat is supplied to the plastics particles contained in the moulding space by heating confinement areas of the moulding space and/or microwaves and/or heat radiation and/or addition of preheated fine-porosity particles.

22. A process according to claim 14, wherein heat is supplied to the plastics particles contained in the moulding space by heating confinement areas of the moulding space and/or microwaves and/or heat radiation and/or addition of preheated fine-porosity particles.

* * * * *